United States Patent
Toporek et al.

(10) Patent No.: US 11,857,379 B2
(45) Date of Patent: *Jan. 2, 2024

(54) FORCE SENSED SURFACE SCANNING SYSTEMS, DEVICES, CONTROLLERS AND METHODS

(71) Applicant: KONINKLIJKE PHILIPS N.V., Eindhoven (NL)

(72) Inventors: Grzegorz Andrzej Toporek, Cambridge, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/093,355

(22) Filed: Jan. 5, 2023

(65) Prior Publication Data

US 2023/0149115 A1 May 18, 2023

Related U.S. Application Data

(63) Continuation of application No. 16/497,963, filed as application No. PCT/EP2018/058379 on Apr. 2, 2018, now Pat. No. 11,564,768.

(Continued)

(51) Int. Cl.
*G06K 9/00* (2022.01)
*A61B 90/00* (2016.01)
(Continued)

(52) U.S. Cl.
CPC .............. *A61B 90/03* (2016.02); *A61B 34/20* (2016.02); *A61B 34/30* (2016.02); *A61B 90/06* (2016.02);
(Continued)

(58) Field of Classification Search
CPC ................................................. A61B 2090/065
See application file for complete search history.

(56) References Cited

U.S. PATENT DOCUMENTS

| 5,794,621 A | 8/1998 | Hogan |
| 2007/0021738 A1 | 1/2007 | Hasser |

(Continued)

FOREIGN PATENT DOCUMENTS

| CN | 103371870 A | 7/2015 |
| DE | 10258579 A1 | 7/2004 |

(Continued)

OTHER PUBLICATIONS

Cash, et al: "Incorporation of a laser range scanner into image-guided liver surgery: Surface acquisition, registration, and tracking", Med. Phys. 30 (7) Jul. 2003.

(Continued)

*Primary Examiner* — Hadi Akhavannik

(57) ABSTRACT

A force sensed surface scanning system (20) employs a scanning robot (41) and a surface scanning controller (50). The scanning robot (41) includes a surface scanning end-effector (43) for generating force sensing data informative of a contact force applied by the surface scanning end-effector (43) to an anatomical organ. In operation, the surface scanning controller (50) controls a surface scanning of the anatomical organ by the surface scanning end-effector (43) including the surface scanning end-effector (43) generating the force sensing data, and further constructs an intraoperative volume model of the anatomical organ responsive to the force sensing data generated by the surface scanning end-effector (43) indicating a defined surface deformation offset of the anatomical organ.

17 Claims, 11 Drawing Sheets

Related U.S. Application Data

(60) Provisional application No. 62/479,815, filed on Mar. 31, 2017.

(51) Int. Cl.
*A61B 34/20* (2016.01)
*A61B 34/30* (2016.01)
*G06T 7/10* (2017.01)

(52) U.S. Cl.
CPC ........ *G06T 7/10* (2017.01); *A61B 2034/2068* (2016.02); *A61B 2090/065* (2016.02); *A61B 2090/378* (2016.02); *G06T 2207/10028* (2013.01); *G06T 2207/30004* (2013.01)

(56) References Cited

U.S. PATENT DOCUMENTS

| | | | | |
|---|---|---|---|---|
| 2008/0123927 | A1* | 5/2008 | Miga | A61B 90/36 382/131 |
| 2012/0316827 | A1* | 12/2012 | Wilkinson | G01B 21/20 702/150 |
| 2013/0063434 | A1* | 3/2013 | Miga | A61B 90/36 382/131 |
| 2013/0138404 | A1* | 5/2013 | Carbonera | G06T 17/205 703/2 |
| 2013/0217997 | A1* | 8/2013 | Byrd | A61B 8/4488 600/409 |
| 2014/0058564 | A1 | 2/2014 | Zhao | |
| 2014/0241600 | A1 | 8/2014 | Mountney | |
| 2014/0303491 | A1 | 10/2014 | Shekhar | |
| 2014/0316234 | A1 | 10/2014 | Waite | |
| 2015/0005089 | A1* | 1/2015 | Davenport | A63B 69/3632 473/223 |
| 2015/0265470 | A1* | 9/2015 | Wilzbach | A61F 9/00821 606/6 |
| 2018/0149460 | A1 | 5/2018 | McGuire | |
| 2019/0374429 | A1* | 12/2019 | Giacometti | A61H 31/005 |

FOREIGN PATENT DOCUMENTS

| | | |
|---|---|---|
| EP | 2179703 A1 | 4/2010 |
| WO | 2012125811 A1 | 9/2012 |

OTHER PUBLICATIONS

Kingham, et al: "Image-guided liver surgery: intraoperative projection of computed tomography images utilizing tracked ultrasound", 2012 International Hepato-Pancreato-Biliary Association.

Herline, et al: "Surface Registration for Use in Interactive, Image-Guided Liver Surgery", Computer Aided Surgery, 5:11-17 (2000).

Haouchine, et al: "Image-guided Simulation of Heterogeneous Tissue Deformation For Augmented Reality during Hepatic Surgery", ISMAR—IEEE International Symposium on Mixed and Augmented Reality 2013.

Rohl, et al: "Fusion of intraoperative force sensing, surface reconstruction and biomechanical modeling", Medical Imaging 2012, SPIE, vol. 8316.

International Search Report and Written Opinion dated Jun. 20, 2018 for International Application No. PCT/EP2018/058379 Filed Apr. 2, 2018.

\* cited by examiner

FORCE SENSED SURFACE SCANNING SYSTEMS, DEVICES, CONTROLLERS AND METHODS

CROSS-REFERENCE TO RELATED APPLICATIONS

This application is a continuation application of U.S. Application No. 16/497,963, filed on Sep. 26, 2019, which is a U.S. National Phase application under 35 U.S.C. § 371 of International Application No. PCT/EP2018/058379 filed Apr. 2, 2018, which claims the benefit of U.S. Patent Application No. 62/479,815, filed on Mar. 31, 2017. These applications are hereby incorporated by reference herein.

FIELD OF THE INVENTION

The inventions of the present disclosure generally relate to systems, devices, controllers and methods for a surface scanning of an anatomical organ (e.g., a liver, a heart, a lung, a brain, a stomach, a spleen, a kidney, a pancreas, a bladder, etc.) for purposes of registering an intraoperative surface scanned volume model of the anatomical-organ with a preoperative image segmented volume model of the anatomical organ.

The inventions of the present disclosure more particularly relate to improving such systems, devices, controllers and methods by implementing a force sensing technology into a robotic-assisted surface scanning of an anatomical organ to thereby enhance a registration of an intraoperative surface scanned volume model of the anatomical organ with a preoperative image segmented volume model of the anatomical organ.

BACKGROUND OF THE INVENTION

Minimally invasive surgical operations may be performed through small, single incision ports in the insufflated abdominal wall. Therefore a line-of-sight via an endoscope to surgical instruments and an outer surface of anatomical organ(s) is provided by endoscopic images. Internal structures of the anatomical organ(s) (e.g., vessels, tumors, etc.) are usually visualized with two-dimensional ("2D") laparoscopic ultrasound (LUS). However, LUS is difficult to interpret in a large anatomical context, especially when the image quality is obscured by tissue abnormalities (e.g. cirrhosis, fatty structures, etc.), by presence of previous oncological therapy (e.g. thermal ablation, transarterial embolization, etc.) and/or by improper acoustic coupling of the LUS to the anatomical organ(s). To improve intraoperative information, a high quality three-dimensional ("3D") imaging modality (e.g., a computer-tomography modality (CT), a magnetic resonance imaging modality (MRD, cone-beam CT (CBCT), etc.) may be fused with the laparoscopic images whereby image registration may provide knowledge of tumor location depth, vicinity of critical anatomical structures, predefined resection plans and other additional information useful for the surgical operation.

Several surface based registration techniques are known in art of the present disclosure for fusing the 3D preoperative images with the intraoperative physical space. These techniques estimate an image-to-patient transformation matrix by matching a surface of the anatomy segmented from the 3D preoperative images with a sparse representation of the same surface acquired during the procedure.

Current techniques as known in the art for intraoperative surface scanning of soft tissue anatomical structure(s) during a surgical procedure utilize either a pre-calibrated tool pointer tracked by external position measurement systems (e.g., optical tracking, electromagnetic tracking, etc.), or external laser range scanners, or 3D multi-view reconstruction from endoscopic images. However, such intraoperative surface scanning is challenging due to unknown tissue properties and large tissue deformation.

More particularly, an accurate anatomy scanning using tracked tool pointers is time-consuming and highly user-dependent. The reproducibility of this method is also hindered by tool calibration and tracking system inaccuracies, errors introduced by the operator when maintaining both constant pressure and contact with the organ surface, and unknown deformation of the soft tissue anatomy during the acquisition.

On the other hand, laser scanning methods require external laser range scanners, which are difficult to integrate into minimally invasive surgical suite, and are inaccurate due to the reflective nature of the organ's surface.

Further a multi-view 3D reconstruction from endoscopic images requires a surface that presents either unique features or the texture and a surface that is not covered by blood.

SUMMARY OF THE INVENTION

To improve upon surface scanning systems, devices, controllers and methods for intraoperative surface scanning of soft tissue anatomical structure(s) during a surgical procedure, the present disclosure provides inventions for constructing an intraoperative scanned volume model of an anatomical organ based upon a sensing of a contact force applied by an surface scanning end-effector of a scanning robot to the anatomical organ whereby the contact force is indicative of a defined surface deformation offset of the anatomical organ.

One embodiment of the inventions of the present disclosure is a force sensed surface scanning system employing a scanning robot and a surface scanning controller.

The scanning robot includes a surface scanning end-effector for generating force sensing data informative of a contact force applied by the surface scanning end-effector to an anatomical organ.

The surface scanning controller is employed for controlling a surface scanning of the anatomical organ by the surface scanning end-effector including the surface scanning end-effector generating the force sensing data, and for constructing an intraoperative volume model of the anatomical organ responsive to the force sensing data generated by the surface scanning end-effector indicating a defined surface deformation offset of the anatomical organ.

A second embodiment of the inventions of the present disclosure is the surface scanning controller employing a scanning commander (133) and a model constructor (134).

The scanning commander (133) is employed for controlling the surface scanning of the anatomical organ by the surface scanning end-effector including the surface scanning end-effector generating force sensing data informative of the contact force applied by the surface scanning end-effector to the anatomical organ.

The model constructor (134) is employed for constructing the intraoperative volume model of the anatomical organ responsive to the force sensing data generated by the surface scanning end-effector indicating a defined surface deformation offset of the anatomical organ.

A third embodiment of the inventions of the present disclosure is a force sensed surface scanning method involving the surface scanning controller controlling a surface scanning of an anatomical organ by the surface scanning end-effector scanning end-effector including the surface scanning end-effector generating force sensing data informative of a contact force applied by the surface scanning end-effector to the anatomical organ.

The force sensed surface scanning method further involves surface scanning controller constructing an intraoperative volume model of the anatomical organ responsive to the force sensing data generated by the surface scanning end-effector indicating a defined surface deformation offset of the anatomical organ.

For purposes of describing and claiming the inventions of the present disclosure:

(1) terms of the art of the present disclosure including, but not limited to, "imaging modality", "scanning robot" and "end-effector" are to be understood as known in the art of the present disclosure and exemplary described herein;

(2) the term "force sensed surface scanning system" broadly encompasses all surface scanning systems, as known in the art of the present disclosure and hereinafter conceived, incorporating the inventive principles of the present disclosure for implementing a force sensing technology into a robotic-assisted surface scanning of an anatomical organ. Examples of known surface scanning systems include, but are not limited to, Philips augmented-reality surgical navigation systems, Philips L10-4lap linear transducer based systems, BrainLab Cranial navigation with navigated pointer tool for surface digitalization, and Pathfindeer surgical navigation system;

(3) the term "force sensed surface scanning method" broadly encompasses all surface scanning methods, as known in the art of the present disclosure and hereinafter conceived, incorporating the inventive principles of the present disclosure for implementing a force sensing technology into a robotic-assisted surface scanning of an anatomical organ. A non-limiting example of known surface scanning method is Philips Pinnacle3;

(4) the term "controller" broadly encompasses all structural configurations of an application specific main board or an application specific integrated circuit for controlling an application of various inventive principles of the present disclosure related to monitoring a folding and/or a twisting of an interventional device within the anatomical lumen as subsequently exemplarily described herein. The structural configuration of the controller may include, but is not limited to, processor(s), computer-usable/computer readable storage medium(s), an operating system, application module(s), peripheral device controller(s), interface(s), bus(es), slot(s) and port(s). The labels "imaging", robot" and "surface scanning" as used herein for the term "controller" distinguishes for identification purposes a particular controller from other controllers as described and claimed herein without specifying or implying any additional limitation to the term "controller".

(6) the term "application module" broadly encompasses a component of a controller consisting of an electronic circuit and/or an executable program (e.g., executable software and/or firmware stored on non-transitory computer readable medium(s)) for executing a specific application. The labels "scanning commander", "model constructor", "model register" and "model fuser" as used herein for the term "module" distinguishes for identification purposes a particular module from other modules as described and claimed herein without specifying or implying any additional limitation to the term "application module"; and (7) the terms "data", and "command" broadly encompasses all forms of a detectable physical quantity or impulse (e.g., voltage, current, or magnetic field strength) as understood in the art of the present disclosure and as exemplary described herein for communicating information and/or instructions in support of applying various inventive principles of the present disclosure as subsequently described herein. Data/command communication between components of the present disclosure may involve any communication method, as known in the art of the present disclosure and hereinafter conceived, including, but not limited to, data/command transmission/reception over any type of wired or wireless medium/datalink and a reading of data/command uploaded to a computer-usable/computer readable storage medium.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

As an improvement of known surface scanning systems, devices, controllers and methods for intraoperative surface scanning of soft tissue anatomical organ(s) during a surgical procedure, the present disclosure provides inventions for constructing an intraoperative scanned volume model of an anatomical organ based upon a sensing of a contact force applied by an surface scanning end-effector of a scanning robot to the anatomical organ whereby the contact force is indicative of a defined surface deformation offset of the anatomical organ.

Figure 1A:
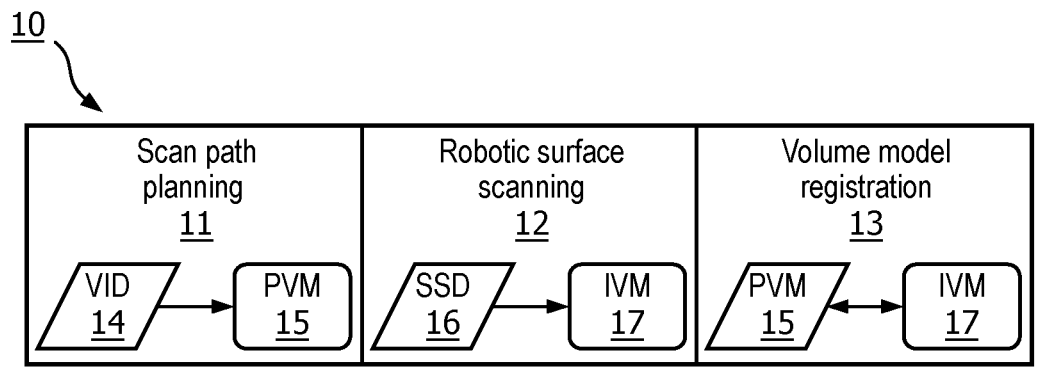
FIG. 1A illustrates an exemplary embodiment of a force sensed surface scanning method in accordance with the inventive principle of the present disclosure.
Figure 1B:
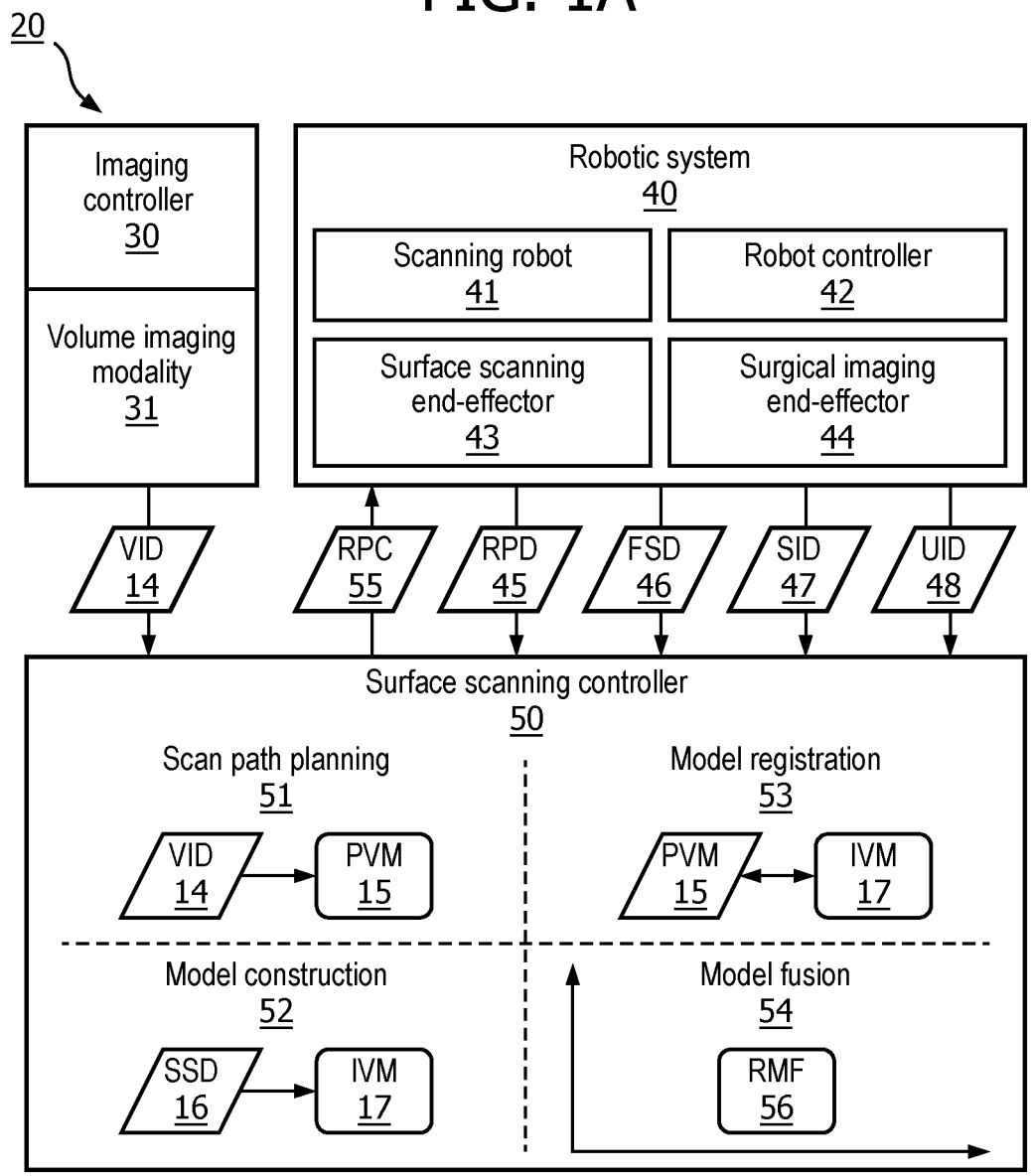
FIG. 1B illustrates an exemplary embodiment of a force sensed surface scanning system in accordance with the inventive principle of the present disclosure.

To facilitate an understanding of the various inventions of the present disclosure, the following description of FIGS. 1A and 1B teaches embodiments of a force sensed surface scanning method 10 and a force sensed surface scanning system 20 in accordance with the inventive principles of the present disclosure. From this description, those having ordinary skill in the art will appreciate how to practice various and numerous embodiments of force sensed surface scanning methods and force sensed surface scanning systems in accordance with the inventive principles of the present disclosure.

Also from this description, those having ordinary skill in the art will appreciate an application of the force sensed surface scanning methods and force sensed surface scanning systems of the present disclosure in support of surgical procedures utilizing fusion of preoperative imaging and intraoperative imaging. Examples of such surgical procedure include, but are not limited to, a cardio-thoracic surgery, a prostatectomy, a splenectomy, a nephrectomy and a hepatectomy.

Referring to FIG. 1B, force sensed surface scanning system 20 employs a volume imaging modality 31, a robotic system 40 and a surface scanning controller 50.

Volume imaging modality 31 is an imaging modality for generating a preoperative volume image of an anatomical region as known in the art of the present disclosure (e.g., a computed tomography imaging, a magnetic resonance imaging, an ultrasound imaging modality, a positron emission tomography imaging, and a single photo emission computed tomography imaging of a thoracic region, a cranial region, an abdominal region or a pelvic region).

Robotic system 40 employs a scanning robot 41, a robot controller 42, a surface scanning end-effector 43 and an ultrasound imaging end-effector 44.

A scanning robot 41 is any type of robot, known in the art of the present disclosure or hereinafter conceived, that is structurally configured or structurally configurable with one or more end-effectors utilized in the performance of a surgical procedure. Further, scanning robot 41 is equipped with pose tracking technology and force sensing technology as known in the art of the present disclosure.

In one exemplary embodiment, a scanning robot 41 is a snake scanning robot equipped with a rotary encoder embedded in each joint of the snake scanning robot for tracking a pose of the snake scanning robot as known in the art of the present disclosure, and further equipped with a force sensor, a pressure sensor, or an optical fiber for sensing a contact force between an end-effector of the snake scanning robot and an anatomical organ as known in the art of the present disclosure.

Robot controller 42 controls a pose of scanning robot 41 within a relevant coordinate system in accordance with robot position commands 55 issued by surface scanning controller 50 as known in the art of the present disclosure.

Surface scanning end-effector 43 is utilized to construct an intraoperative scanned volume model 17 of the anatomical region in accordance with the inventive principles of the present invention as will be further explained herein. In practice, surface scanning end-effector 43 may be any type of end-effector having a calibration scan reference thereon as known in the art of the present disclosure. In exemplary embodiments, surface scanning end-effector 43 may include mount holding a tool pointer having a spherical distal tip serving as a calibrated scanning reference, or may include a mount holding an ultrasound laparoscope having an ultrasound transducer serving as a calibrated scanning reference.

Surgical imaging end-effector 44 is utilized to intraoperatively image an external surface and/or internal structures within the anatomical organ in support of a surgical procedure as known in the present disclosure. In an exemplary embodiment, surgical imaging end-effector 44 may be an ultrasound laparoscope, which may also serve as surface scanning end-effector 43.

In practice, surface scanning end-effector 43 is mounted onto scanning robot 41 whereby robot controller 42 controls scanning robot 41 in accordance with robot position commands 55 from surface scanning controller 50 to implement a robotic surface scanning 12 of force sensed surface scanning method 10 of FIG. 1A as will be further explained herein. Subsequently, surgical imaging end-effector 44 is mounted onto scanning robot 41 whereby robot controller 42 controls scanning robot 41 in accordance with interactive or planned commands from an operator of robotic system 40 during a surgical procedure as will be further explained herein.

Alternatively in practice, surface scanning end-effector 43 is affixed to scanning robot 41 whereby robot controller 42 controls scanning robot 41 in accordance with robot position commands 55 from surface scanning controller 50 to implement a robotic surface scanning 12 of force sensed surface scanning method 10 of FIG. 1A as will be further explained herein. Subsequently, surgical imaging end-effector 44 is affixed to or mounted onto an additional scanning robot 41 whereby robot controller 42 controls the additional scanning robot 41 in accordance with interactive or planned commands from an operator of robotic system 40 during a surgical procedure as will be further explained herein.

Surface scanning controller 50 controls an implementation of force sensed surface scanning method 10 (FIG. 1A) of the present disclosure as will now be described herein.

Referring to FIGS. 1A and 1B, force sensed surface scanning method 10 involves a scan path planning phase 11, a robotic surface scanning phase 12 and a volume model registration phase 13.

Prior to a path planning phase 11 of method 10, an imaging controller 30 is operated for controlling a generation by a volume imaging modality 31 of a preoperative volume image of an anatomical region as known in the art of the present disclosure (e.g., a computed tomography imaging, a magnetic resonance imaging, an ultrasound imaging modality, a positron emission tomography imaging, and a single photo emission computed tomography imaging of a thoracic region, a cranial region, an abdominal region and a pelvic region).

Path planning phase 11 of method 10 encompasses a communication of volume image data 14 representative of the preoperative volume image of the anatomical organ to surface scanning controller 50 by any communication technique known in the art of the present disclosure (e.g., a data upload or a data streaming). Surface scanning controller 50 processes volume image data 14 to generate a preoperative image segmented volume model 15 of an anatomical organ within the anatomical region as known in the art of the present disclosure (e.g., a segmented volume model of a liver, a heart, a lung, a brain, a stomach, a spleen, a kidney, a pancreas, a bladder, etc.).

Alternatively, imaging controller 30 may process volume image data 14 to generate preoperative image segmented volume model 15 of the anatomical organ as known in the art of the present disclosure whereby path planning phase 11 of method 10 encompasses a communication of preoperative image segmented volume model 15 of the anatomical organ to surface scanning controller 50 by any communication technique known in the art of the present disclosure (e.g., a data upload or a data streaming).

Path planning phase 11 of method 10 further encompasses surface scanning controller 50 executing a scan path planning 51 involving a definition of a path along one or more segments or an entirety of a surface of preoperative image segmented volume model 15 of the anatomical organ as known in the art of the present disclosure.

In one embodiment of scan path planning 51, surface scanning controller 50 implements an operator or systematic delineation as known in the art of the present disclosure of a line sampling scan path on preoperative image segmented volume model 15 of the anatomical organ involving a continuous contact between surface scanning end-effector 43 and the anatomical organ as surface scanning end-effector 43 is traversed along one or more lines over a surface segment or an entire surface of preoperative image segmented volume model 15 of the anatomical organ.

Figure 2A:
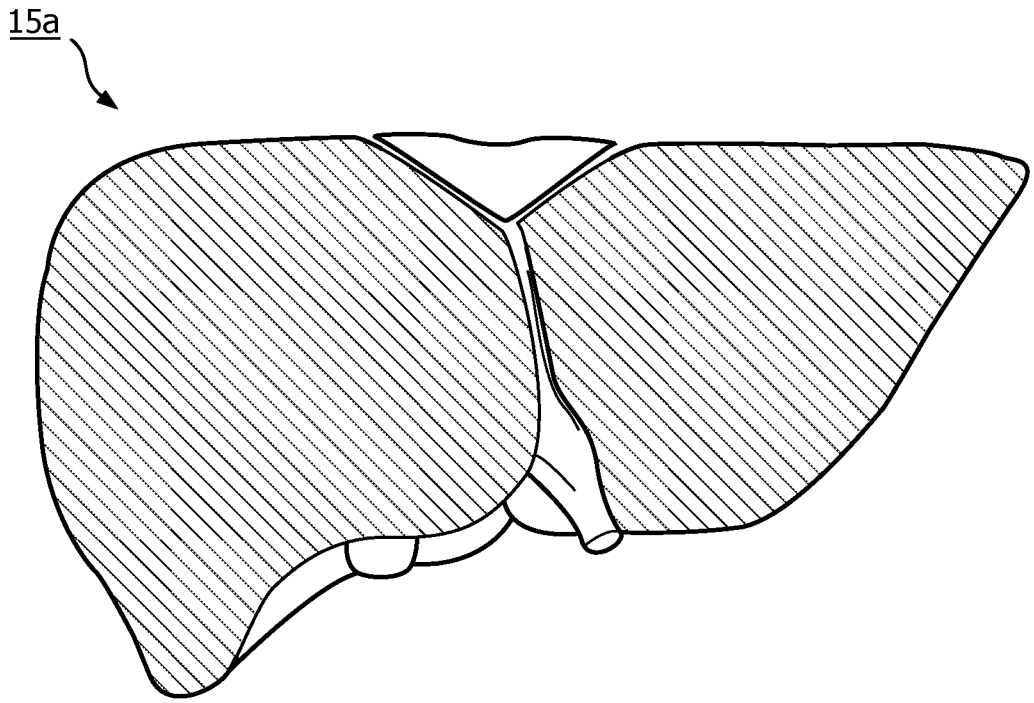
FIGS. 2A and 2B illustrate exemplary scanned path planning in accordance with the inventive principles of the present disclosure.

For example, FIG. 2A illustrates an exemplary delineation of a line sampling scan path 15a including a plurality of lines traversing the surface of a preoperative image segmented volume model of a liver. In practice, the lines may be disconnected as shown or connected to any degree by an operator or system delineation of path 15a.

Alternatively in practice, a line sampling scan path may be defined independent of the preoperative image segmented volume. For example, the line sampling scan path may be a defined as a geometric pattern (e.g., a spiral pattern, a zigzag pattern, etc.) or as a random pattern (e.g., a white noise sampling scheme) or a combination thereof.

In a second embodiment of scan path planning 51, surface scanning controller 50 implements an operator or systematic delineation as known in the art of the present disclosure of a point sampling scan path on preoperative image segmented volume model 15 of the anatomical organ involving a periodic contact between surface scanning end-effector 43 and the anatomical organ as surface scanning end-effector 42 is traversed over a surface segment or an entire surface of preoperative image segmented volume model 15 of the anatomical organ.

Figure 2B:
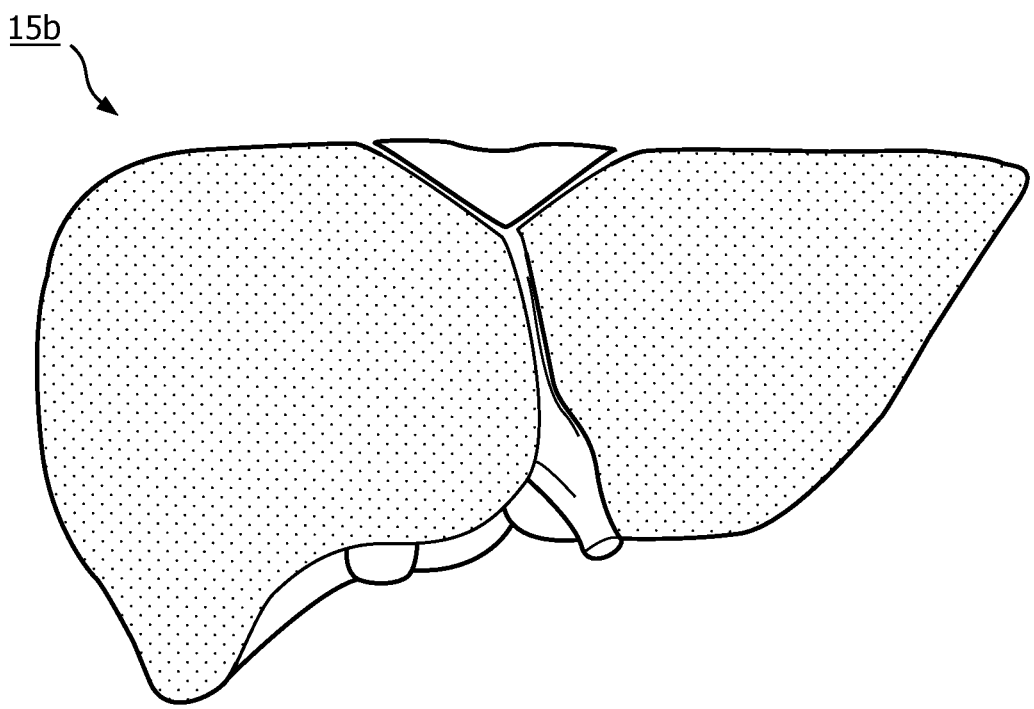

For example, FIG. 2B illustrates an exemplary a delineation of a point sampling scan path 15b including a plurality of points marked on a surface of a preoperative image segmented volume model of a liver. In practice, as designed by an operator or system delineation of path 15b, the points may be arranged in a uniform pattern as shown or in a non-uniform pattern.

Alternatively in practice, a point sampling scan path may be defined independent of the preoperative image segmented volume. For example, the line sampling scan path may be a defined as a geometric pattern (e.g., a spiral pattern, a zigzag pattern, etc.) or as a random pattern (e.g., a white noise sampling scheme) or a combination thereof.

Further in practice, scan path planning 51 may also involve any combination of a line sampling scan path and a point sampling scan path delineated on preoperative image segmented volume model 15 of the anatomical organ.

Additionally in practice, scan path planning 51 may be omitted for surface scanning controller 50 or not used by surface scanning controller 50 for a particular procedure. In this scenario, an operator of system 20 may control a navigation of scanning robot 41 in implementing an operator defined sampling scan path.

Still referring to FIGS. 1A and 1B, robotic surface scanning phase 12 of method 10 encompasses an image guidance of surface scanning end-effector 43 in proximity of the anatomical organ whereby surface scanning controller 50 is operated to issue robot position commands 55 to robot controller 42 for controlling a navigation of surgical scanning end-effector 43 relative to the anatomical organ in accordance with the planned sampling scan path delineated on preoperative image segmented volume model 15 of the anatomical organ.

More particularly, to facilitate a model registration 53 in accordance with the inventive principles of the present disclosure as will be further described herein, robotic system 40 communicates surface sensing data 16 to surface scanning controller 50 whereby surface scanning controller 50 implements a model construction 52 of an inoperative volume model 17 of the anatomical organ in accordance with the inventive principles of the present disclosure as will be further described herein.

More particularly, surface sensing data 16 includes robotic position data 45 communicated by robot controller 42 to surface scanning controller 50 whereby robot position data 45 is informative of a current pose of scanning robot 41 within a coordinate system registered to the anatomical organ or preoperative segmented volume model as known in the art of the present disclosure.

Surface sensing data 16 further includes force sensing data 46 informative of a contact force applied by the surface scanning end-effector 43 to the anatomical organ, and for imaging embodiments of surface scanning end-effector 43, surface sensing data 16 further includes scan image data 47 representative of a current image slice of the anatomical image.

Surface scanning controller 50 processing robot position data 45, force sensing data 46 and scan image data 47 (if applicable) to construct an inoperative volume model 17 of the anatomical organ based on a physical behavior of a soft tissue of an anatomical organ under a minor deformation by scanning surface end-effector 42 (e.g., a tissue deformation in nanometers).

Specifically, model construction 52 is premised on an assumption that the physical behaviour soft tissue of an anatomical organ under a minor deformation is both linearly elastic and one-dimensional. Under such conditions, an offset between undeformed anatomical tissue and deformed anatomical tissue may be calculated using the equation u=f/k, where u is a tissue displacement (offset), f is the sensed contact force between surface scanning end effector 43 and the deformed anatomical tissue, and k is a parameter describing viscoelastic properties of the anatomical organ.

From the assumption, model construction 52 involves a designation of a defined scanning force parameter $f_{DO}$ and of a defined visocleastic property parameter k whereby a surface deformation offset $u_{SDO}$ may be calculated to support the construction of the inoperative volume model 17 of the anatomical organ as will be further explained herein.

In one embodiment of model construction 52, an operator of surface scanning controller 50 via input devices and/or graphical interfaces provides or selects a visocleastic property parameter k as a constant value representative viscoelastic properties of the subject anatomical organ, and further provides or selects a scanning force parameter $f_{DC}$ at which the surface of the anatomical organ will be scanned (e.g., a contact force in meganewtons). A surface deformation offset $u_{SDO}$ is calculated from the provided/selected visocleastic property parameter k and scanning force parameter $f_{DC}$ to support the construction of the inoperative volume model 17 of the anatomical organ.

Alternatively, the present disclosure recognizes a viscoelastic behavior of a soft tissue of an anatomical organ under deformation may be a very complex process. First, the viscoelastic parameters for any unevenly distributed force may be described by a multi-dimensional matrix, which takes into account the direction of the force and topology of the surface. Second, a linearity of the deformation holds true only for very small deformations (e.g., in the order of nanometers). Third, a viscoelastic property parameters k of the soft tissue of the anatomical organ may be either unknown due to tissue abnormalities or due to patient-specific anatomical characteristics. Thus, in a second embodiment of model construction 52, surface deformation offset $u_{SDO}$ is empirically defined as will be further explained herein.

Still referring to FIGS. 1A and 1B, as surface scanning controller 50 controls a navigation of surgical scanning end-effector 43 relative to the anatomical organ in accordance with the planned sampling scan path delineated on preoperative image segmented volume model 15 of the anatomical organ, robotic surface scanning phase 12 of method 10 further encompasses surface scanning controller 50 recording each positon of the calibrated scanned reference of scanning surface end-effector 43 that correspond to a contact force applied by surface scanning end-effector 43 to the anatomical organ equaling scanning force parameter $f_{DC}$. In practice, the sensed contact form equaling the scanning force parameter $f_{DC}$ may be enforced with an acceptable margin of error.

Each recorded positon of the calibrated scanned reference of scanning surface end-effector 43 is deemed a digitized model point suitable for a generation of a sparse point cloud representation of the anatomical organ on the assumption of a uniform deformation offset of each recorded position of a digitized model point.

In practice, as will be further explained herein, a line sampling scan path generates a sparse point cloud representation of the anatomical organ in view of a subset of positons of the calibrated scanned reference of scanning surface end-effector 43 corresponding to a contact force applied by surface scanning end-effector 43 to the anatomical organ equaling scanning force parameter $f_{DC}$ and further in view a subset of positons of the calibrated scanned reference of scanning surface end-effector 43 failing to correspond to a contact force applied by surface scanning end-effector 43 to the anatomical organ equaling scanning force parameter $f_{DC}$.

Also in practice, as will be further explained herein, a point sampling scan path generates a sparse point cloud representation of the anatomical organ based on the spatial delineation of the points on preoperative image segmented volume model 15 of the anatomical organ.

For non-imaging embodiments of scanning surface end-effector 43, robotic surface scanning phase 12 of method 10 further encompasses surface scanning controller 50 constructing intraoperative volume model 17 as a mesh created from the sparse point cloud representation via any mesh construction technique known in the art of the present disclosure (e.g., a Delaunay triangulation).

Due to the defined deformation offset, the mesh will have a comparable shape to a shape of the preoperative image segmented volume model 15 of the anatomical organ for registration purposes, but the mesh will have a not necessarily have a comparable size to a size of the preoperative image segmented volume model 15 of the anatomical organ. While not necessary for most registration processes, to achieve comparable sizes, surface scanning controller 50 may further calculate normal vectors at each vertex as a function of the defined deformation offset via any mesh normalization technique known in the art of the present disclosure (e.g., a Mean Weight Equal), and displace each point of the mesh in a direction of the associated normal vector to increase the size yet maintain the shape of the mesh.

For imaging embodiments of scanning surface end-effector 43, robotic surface scanning phase 12 of method 10 further encompasses surface scanning controller 50 stitching images associated with each point of the mesh, unsized or sized to thereby render intraoperative volume model 17 as an image of the anatomical organ. In practice, while stitching images associated with each point of the mesh, surface scanning controller 50 may interpolate images missing from the mesh due to unrecorded positions of the calibrated scanned reference of scanning surface end-effector 43.

Figure 3A:
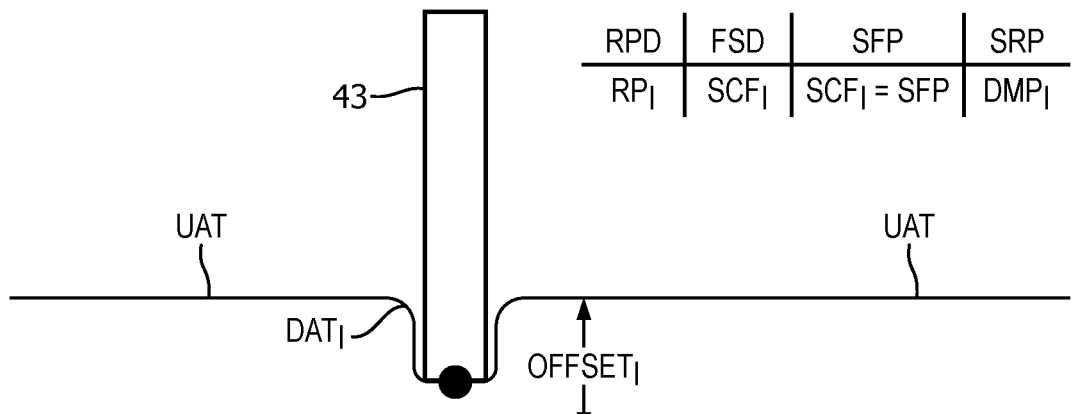
FIGS. 3A-3C illustrate an exemplary surface scanning of an anatomical organ by a surface scanning end-effector in accordance with the inventive principle of the present disclosure.
Figure 3B:
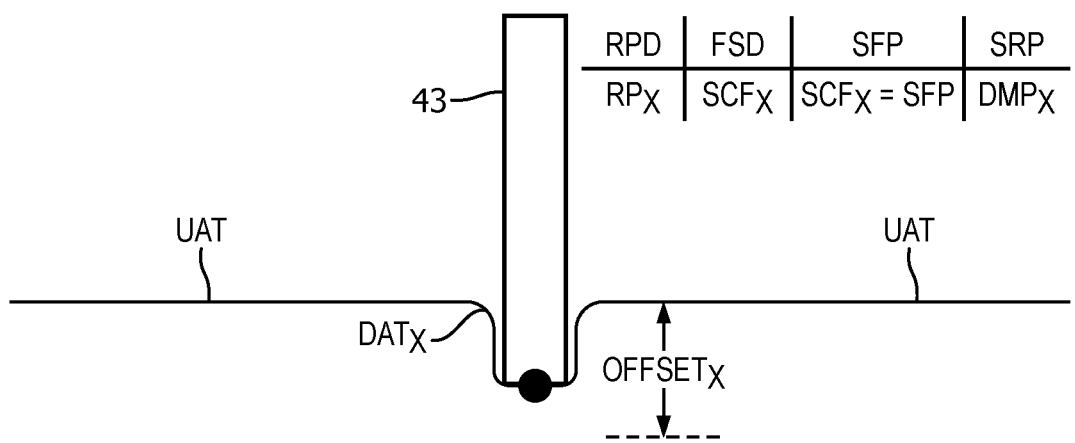
Figure 3C:
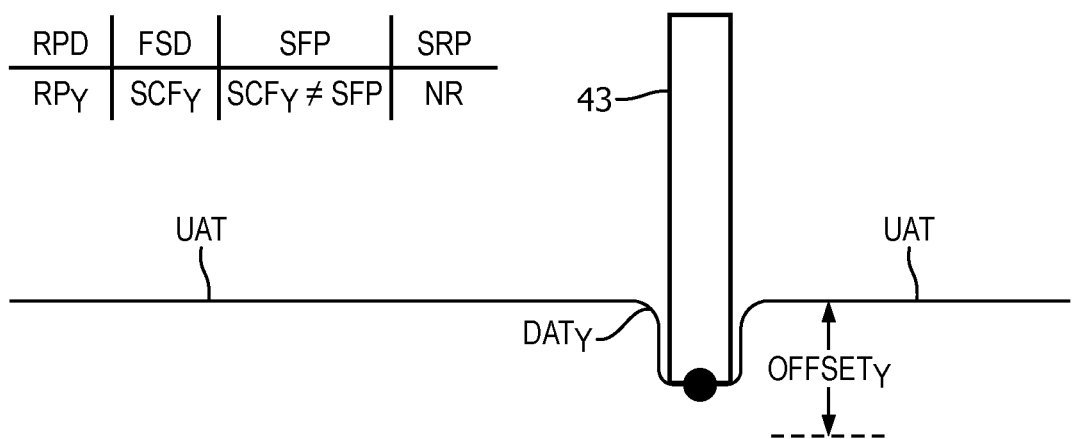

To facilitate an understanding of the various inventions of the present disclosure, the following description of FIGS. 3A-3C illustrates exemplary recorded positions of digitize model points in accordance with the inventive principles of the present disclosure. From this description, those having ordinary skill in the art will further appreciate how to practice various and numerous embodiments of force sensed surface scanning methods and force sensed surface scanning systems in accordance with the inventive principles of the present disclosure.

Referring to FIG. 3A, surface scanning end-effector 43 is shown deforming an anatomical organ prior to a scanning of the surface of the anatomical organ. More particularly, surface scanning controller 50 controls a positioning of scanning end-effector 43 relative to the anatomical organ to initially apply a contact force unto the tissue of the anatomical organ resulting in an $OFFSET_1$ between undeformed anatomical tissue UAT and deformed anatomical tissue $DAT_1$. The positioning of scanning end-effector 43 is adjusted until a sensed contact force $SCF_1$ per force sensing data FSD equals a desired contact force DCF whereby $OFFSET_1$ between undeformed anatomical tissue UAT and deformed anatomical tissue $DAT_1$ is deemed to equate the defined surface deformation offset $u_{SDO}$ of the anatomical organ as previously described herein. Consequently, from a corresponding robot positon $RP_1$ per robot position data 45, surface scanning controller 50 records calibrated scanned reference positon SRP of surface scanning end-effector 43 represented by the black dot as the initial digitized model point $DMP_1$.

During a scanning of the surface of the anatomical organ, FIG. 3B illustrates a repositioning of scanning end-effector 43 to a robot positon $RP_X$ relative to the anatomical organ resulting in $OFFSET_X$ between undeformed anatomical tissue UAT and deformed anatomical tissue $DAT_X$ with a sensed contact force $SCF_X$ per force sensing data FSD equals a desired contact force DCF, and FIG. 3B illustrates a repositioning of scanning end-effector 43 to a robot positon $RP_Y$ relative to the anatomical organ resulting in $OFFSET_Y$ between undeformed anatomical tissue UAT and deformed anatomical tissue $DAT_Y$ with a sensed contact force $SCF_Y$ per force sensing data FSD that does not equal a desired contact force DCF.

For point sampling scan path embodiments, the repositioning of scanning end-effector 43 is adjusted until a sensed contact force SCF per force sensing data FSD equals a desired contact force DCF as shown in FIG. 3B whereby $OFFSET_X$ between undeformed anatomical tissue UAT and deformed anatomical tissue $DAT_X$ is deemed to equate the defined surface deformation offset $u_{SDO}$ of the anatomical organ as previously described herein. Consequently, from a corresponding robot positon $RP_X$ per robot position data 45, surface scanning controller 50 records calibrated scanned reference positon SRP of surface scanning end-effector 43 represented by the black dot as an additional digitized model point $DMP_X$. This process is repeated for each point in the point sampling scan path.

For line sampling scan path embodiments, as surface sensing end-effector 43 is traversed along a line over the surface of the anatomical organ, surface scanning controller 50 will digitize robot positions $RP_X$ as shown in FIG. 3B and will not digitize robot positions $RP_Y$ as shown in FIG. 3C or any other robot positon failing to sense a contact force equaling the scanning force parameter SFP.

The result for either embodiment is a spare cloud representation of the anatomical organ facilitating of an unsized or resized mesh creation of inoperative volume model 17.

Referring back to FIGS. 1A and 1B, volume model registration 13 of method 10 encompasses surface scanning controller 50 implementing a model registration 53 of preoperative segmented volume model 15 and intraoperative volume model 17 via a registration technique as known in the art of the present disclosure.

In mesh embodiments of intraoperative volume model 17, surface scanning controller 50 may execute a point-by-point registration technique for registering preoperative segmented volume model 15 and intraoperative volume model 17. Examples of such a point-by-point registration technique include, but are not limited to, a rigid or non-rigid Iterative Closer Point (ICP) registration, a rigid or non-rigid Robust Point Matching (RPM) registration and a particle filter based registrations.

In stitched image embodiments of intraoperative volume model 17, surface scanning controller 50 may execute an image registration technique for registering preoperative segmented volume model 15 and intraoperative volume model 17. Examples of such a point-by-point registration technique include, but are not limited to, an internal anatomical landmark based image registration (e.g., bifurcations or calcifications), an internal implanted marker based image registration and a mutual information based image registration.

Still referring FIGS. 1A and 1B, upon completion of the scanning process, surface scanning controller 50 may implement a model fusion 54 based on model registration 53 as known in the art of the present disclosure whereby a registered model fusion 56 may be displayed within an applicable coordinate system as symbolically shown.

In one embodiment, registered model fusion 56 includes an overlay of preoperative segmented volume model 15 onto intraoperative volume model 17.

In another embodiment, registered model fusion 56 includes an overlay of preoperative segmented volume model 15 onto the anatomical organ as registered to the coordinate system of robotic system 40.

Figure 4:
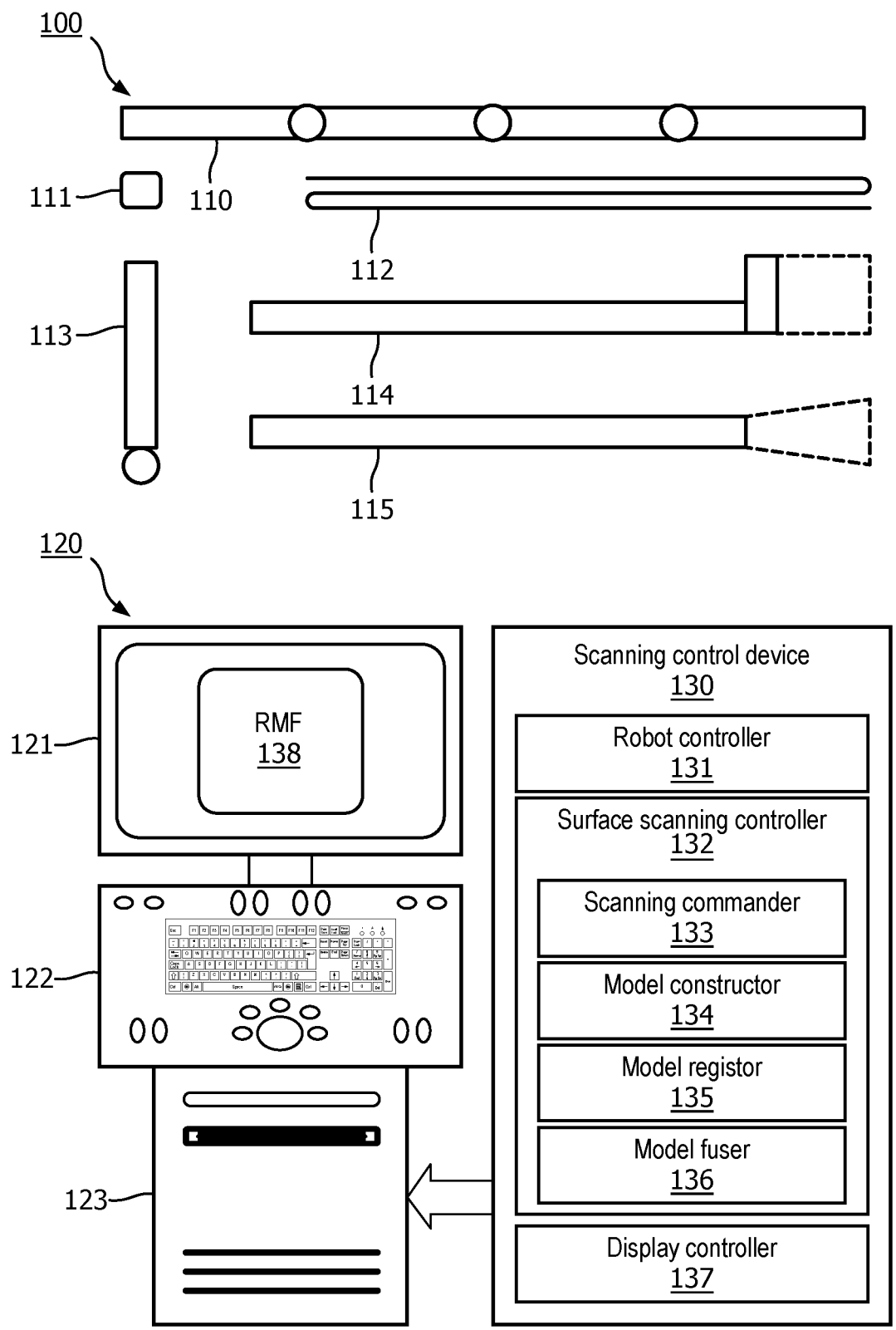
FIG. 4 illustrates an exemplary embodiment of the force sensed surface scanning system of FIG. 1B in accordance with the inventive principle of the present disclosure.
Figure 5:
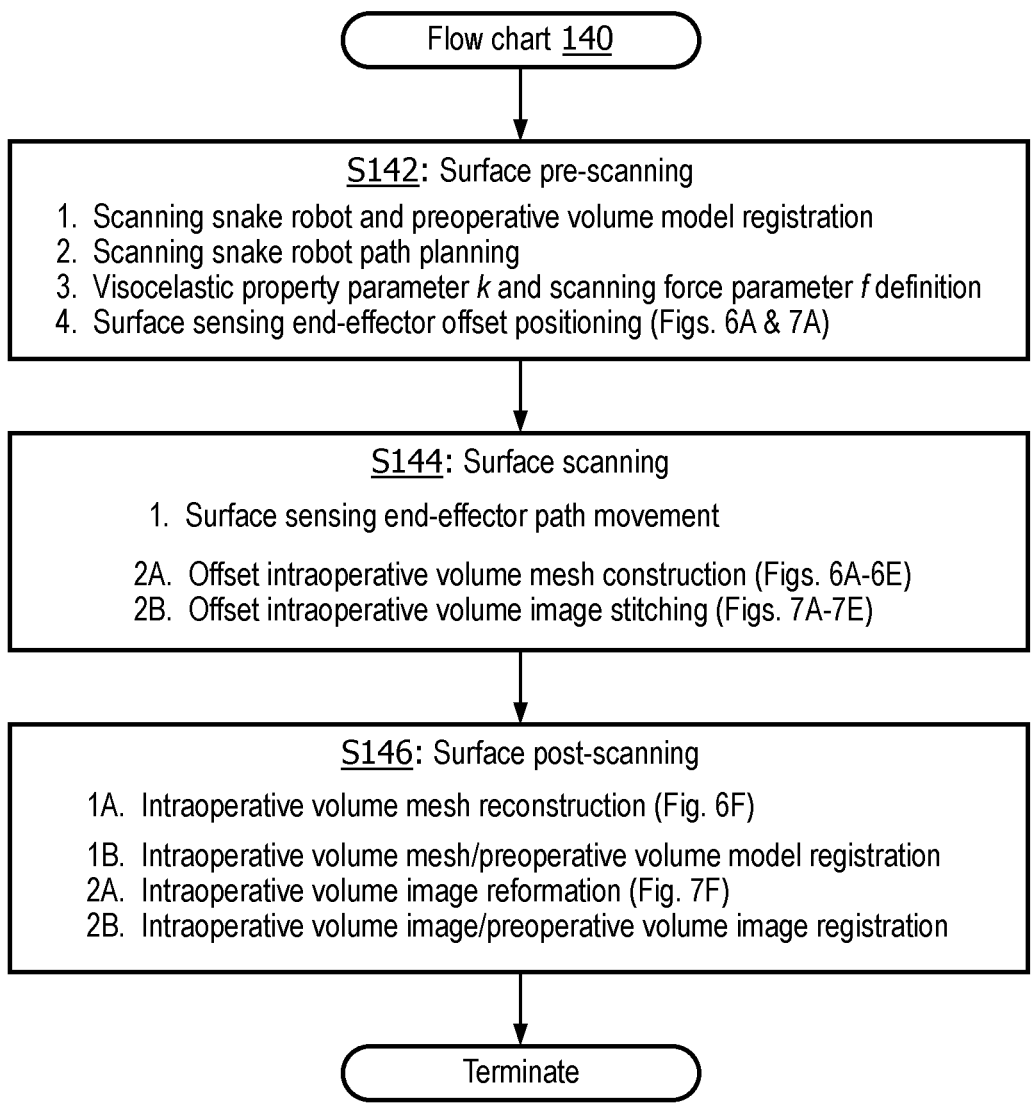
FIG. 5 illustrates a flowchart representative of an exemplary embodiment of the force sensed surface scanning method of FIG. 1A in accordance with the inventive principle of the present disclosure.

To facilitate an understanding of the various inventions of the present disclosure, the following description of FIGS. 4 and 5 teaches additional embodiments of a force sensed surface scanning system 100 and a force sensed surface scanning system 140 in accordance with the inventive principles of the present disclosure. From this description, those having ordinary skill in the art will further appreciate how to practice various and numerous embodiments of force sensed surface scanning methods and force sensed surface scanning systems in accordance with the inventive principles of the present disclosure.

Referring to FIG. 4, force sensed surface scanning system 100 employs a snake scanning robot 110, a tool pointer 113, an ultrasound laparoscope 114 and an endoscope 115.

For scanning purposes, tool pointer 113 or ultrasound laparoscope 114 may be mounted onto snake scanning robot 110 as known in the art of the present disclosure.

Snake scanning robot 110 is equipped with either force/pressure sensor(s) 111 and/or optical fiber(s) 112 for sensing a contact force applied by a mounted tool pointer 113 or ultrasound laparoscope 114 to an anatomical organ as known in the art of the pressure disclosure.

Endoscope 115 is mountable on additional snake scanning robot 110 for purposes of viewing a positioning of tool pointer 113 or ultrasound laparoscope 114 in proximity of a surface of an anatomical organ.

Force sensed surface scanning system 100 further employs a workstation 120 and a scanning control device 130.

Workstation 120 includes a known arrangement of a monitor 121, a keyboard 122 and a computer 123 as known in the art of the present disclosure. Scanning control device 130 employs a robot controller 131, a surface scanning controller 132 and a display controller 137, all installed on computer 123.

In practice, robot controller 131, surface scanning controller 132 and display controller 137 may embody any arrangement of hardware, software, firmware and/or electronic circuitry for implementing a force sensed surface scanning method as shown in FIG. 5 in accordance with the inventive principles of the present disclosure as will be further explained herein.

In one embodiment, robot controller 131, surface scanning controller 132 and display controller 137 each may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In a non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent.

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage may further store one or more application modules in the form of executable software/firmware.

More particularly, still referring to FIG. 4, robot controller 131 includes application module(s) for controlling a navigation of snake scanning robot 100 within a robotic coordinate system as known in the art of the present disclosure, and display controller 137 includes application module(s) for controlling a display of images, graphical user interfaces, etc. on monitor 120 as known in the art of the present disclosure.

Surface scanning controller 132 includes application modules in the form of a scanning commander (133) 133, a model constructor (134) 134, a model registor 137 and a model fuser 136 for controlling the implementation of the force sensed surface scanning method as shown in FIG. 5 in accordance with the inventive principles of the present disclosure as will be further explained herein.

In practice, scanning control device 130 may be alternatively or concurrently installed on other types of processing devices including, but not limited to, a tablet or a server accessible by workstations and tablets, or may be distributed across a network supporting an execution of a surgical procedure utilizing a force sensed surface scanning method of the present disclosure as shown in FIG. 5.

Also in practice, controllers 131, 132 and 135 may be integrated components, segregated components or logically partitioned components of scanning control device 130.

FIG. 5 illustrates a flowchart 140 representative of a force sensed surface scanning method in accordance with the inventive principles of the present disclosure that is implemented by application modules 133-136 of surface scanning controller 132 as will now be described herein.

Referring to FIG. 5, a stage S142 of flowchart 140 encompasses pre-scanning activities implemented by scanning commander 133 (FIG. 4). These pre-scanning activities include, but are not limited to, 1. scanning commander 133 controlling a registration of snake scanning robot 110 and a preoperative segmented volume model registration as known in the art;
2. scanning commander 133 controlling a planning of a sampling scanning path for snake scanning robot 110 as previously described herein in connection with the description of FIGS. 1A and 1B, particularly a line sampling scanning path or a point sampling scanning path;
3. scanning commander 133 controlling a graphical user interface for an operator provision or an operator selection of viscoelastic property parameter k and scanning force parameter f, and
4. scanning commander 133 controlling an initial offset positioning of a surface sensing end-effector, such as, for example, an initial positioning of tool pointer 113 as shown in FIG. 6A or an initial positioning of ultrasound laparoscope 114 as shown in FIG. 7A.

More particularly, a defined surface deformation offset u is calculated from the provided/selected viscoelastic property parameter k and scanning force parameter f whereby scanning parameter 133 controls the initial offset positioning of the surface sensing end-effector to equate a sensed contact force to scanning force parameter f to thereby achieve a defined surface deformation offset u between an undeformed anatomical tissue and a deformed anatomical tissue of the anatomical organ as previously described herein.

Figure 6A:
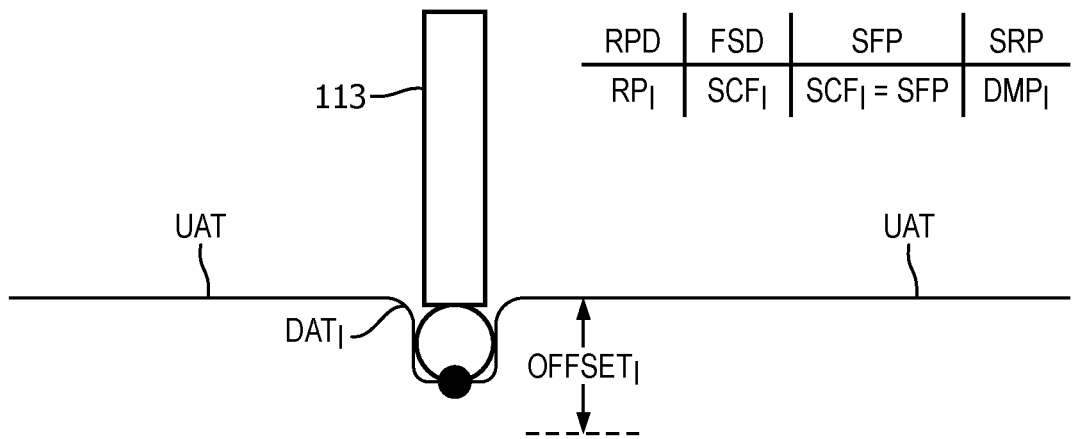
FIGS. 6A-6F illustrate an exemplary surface scanning of an anatomical organ by a pointer tool in accordance with the inventive principle of the present disclosure.
Figure 7A:
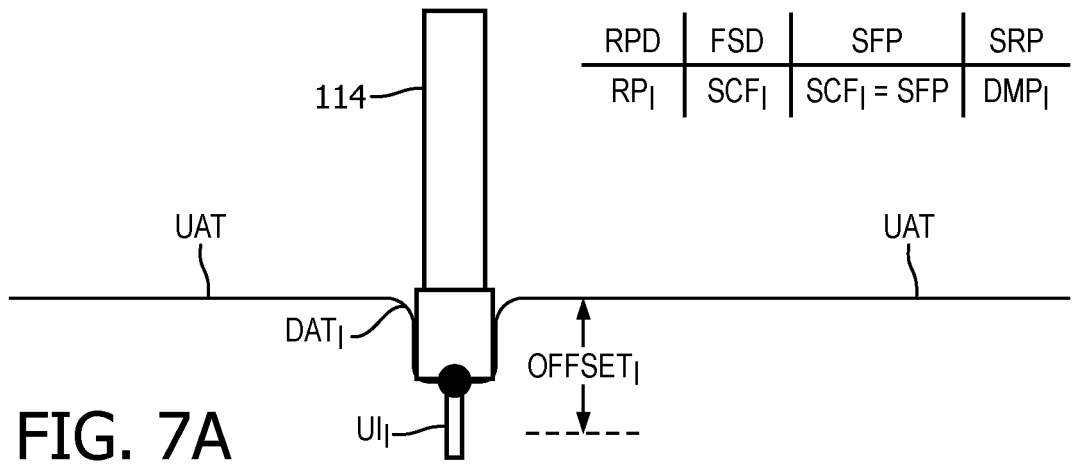
FIGS. 7A-7F illustrate an exemplary surface scanning of an anatomical organ by an ultrasound laparoscope in accordance with the inventive principle of the present disclosure.

For embodiments whereby viscoelastic property parameter k is known, defined surface deformation offset u may be empirically defined by:

1. scanning commander 133 controlling a graphical user interface for operator control of an initial offset positioning of a surface sensing end-effector at a selected non-zero sensed control force, such as, for example, an initial positioning of tool pointer 113 as shown in FIG. 6A or an initial positioning of ultrasound laparoscope 114 as shown in FIG. 7A; and
2. scanning commander 133 retracting the surface sensing end-effector until such time the sensed control force is zero; and
3. scanning commander 133 defining scanned force parameter f as the selected non-zero sensed control force associated with the initial offset positioning of the surface sensing end-effector, and further defining surface deformation offset u as the retraction distance of the surface sensing end-effector.

Alternatively in practice, a sampling scan path may be defined independent of the preoperative image segmented volume during stage S142, thereby omitting a requirement to register snake scanning robot 110 to the preoperative segmented volume model. For example, the sampling scan path may be a defined as a geometric pattern (e.g., a spiral pattern, a zigzag pattern, etc.) or as a random pattern (e.g., a white noise sampling scheme) or a combination thereof. For such an alternative embodiment of stage S142, a surface of the anatomical organ is exposed via a surgical port, and the snake scanning robot 110 is inserted through the surgical port to the surface of the anatomical organ until reaching the initial offset positioning of the surface sensing end-effector or a position for an empirical definition of the surface deformation offset u. Thereafter snake scanning robot 110 is manually or controller operated to follow a predefined geometric pattern or to randomly traverse the surface of the anatomical organ or a combination thereof.

Still referring to FIG. 5, a stage S144 of flowchart 140 encompasses scanning activities implemented by scanning commander 133 (FIG. 4) and model constructor (134) 134 (FIG. 4). These scanning activities include, but are not limited to, 1. scanning commander 133 controlling a navigation of snake scanning robot 110 relative to the anatomical organ in accordance with the planned sampling scan path as previously described herein in connection with the description of FIGS. 1A and 1B; and
2A. model constructor 134 constructing an intraoperative volume mesh as previously described herein in connection with the description of FIGS. 1A and 1B, such as for example, an intraoperative volume mesh 170 shown in FIG. 6E; or
2B. model constructor 134 stitching an intraoperative volume image as previously described herein in connection with the description of FIGS. 1A and 1B, such as for example, an intraoperative volume image 180 shown in FIG. 7E.

Figure 6B:
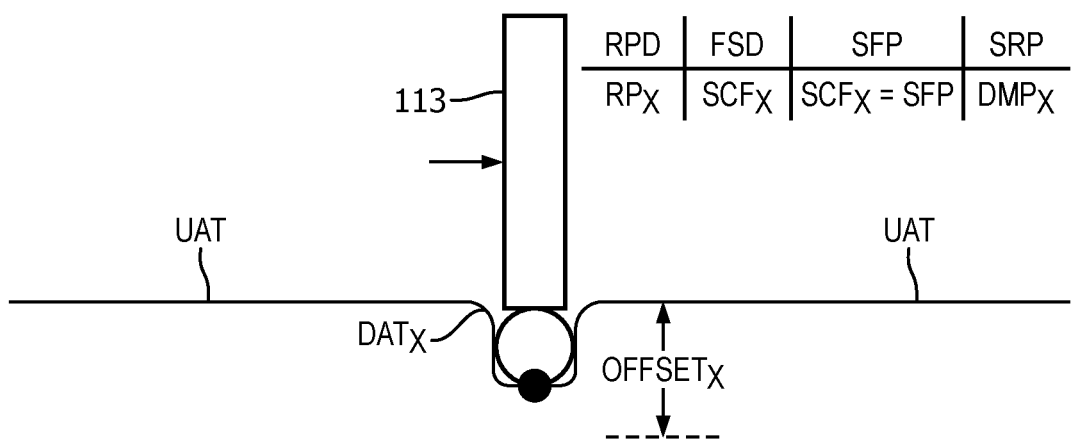
Figure 6C:
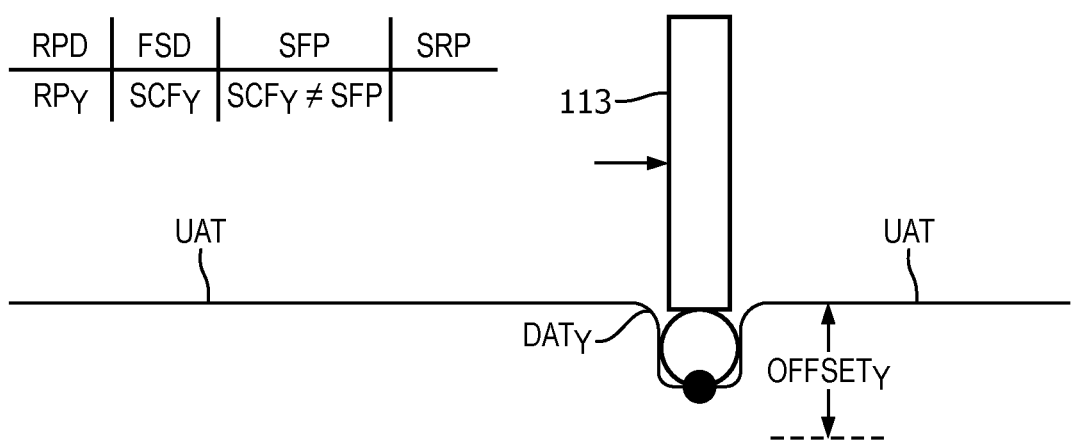

More particular to embodiments of stage S144 utilizing tool pointer 113, the navigation of snake scanning robot 110 will result in a digitization of sample points indicating a sensed contact force equating scanned force parameter f as exemplary shown in FIG. 6B and a non-digitization of sample point indicating a sensed contact force not equating scanned force parameter f as exemplary shown in FIG. 6C.

Figure 6D:
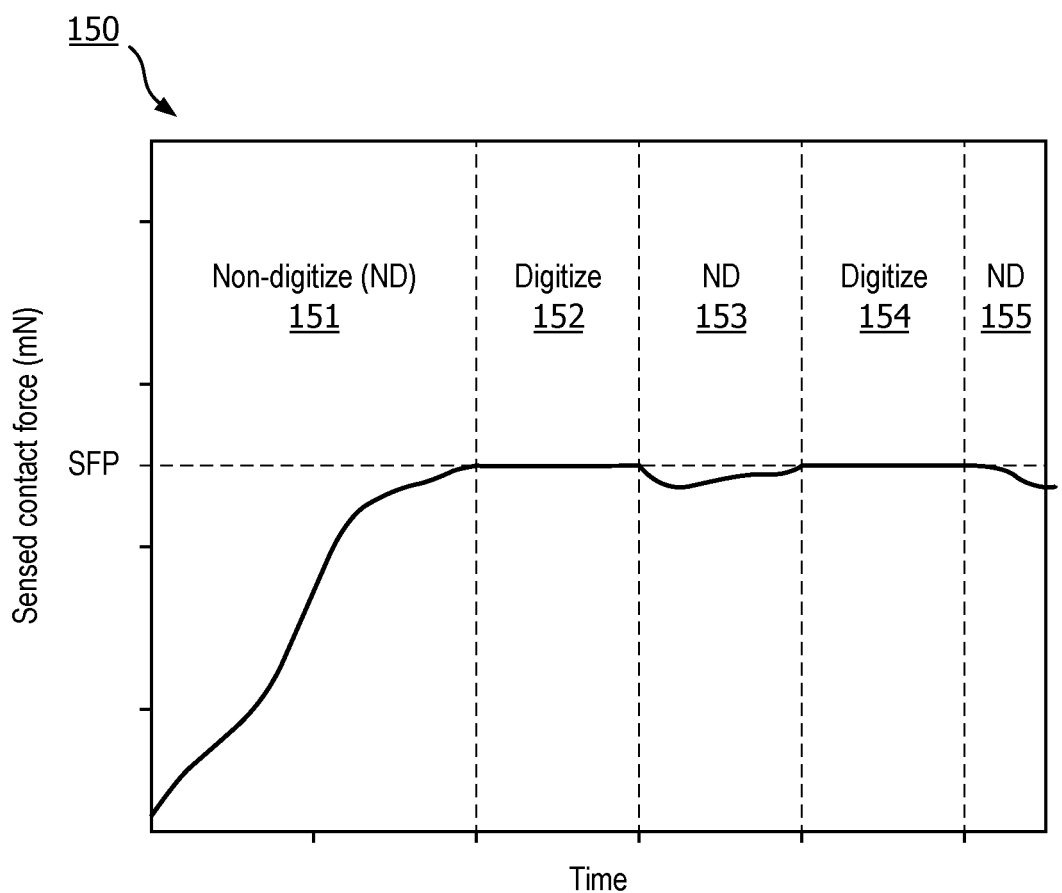
Figure 6E:
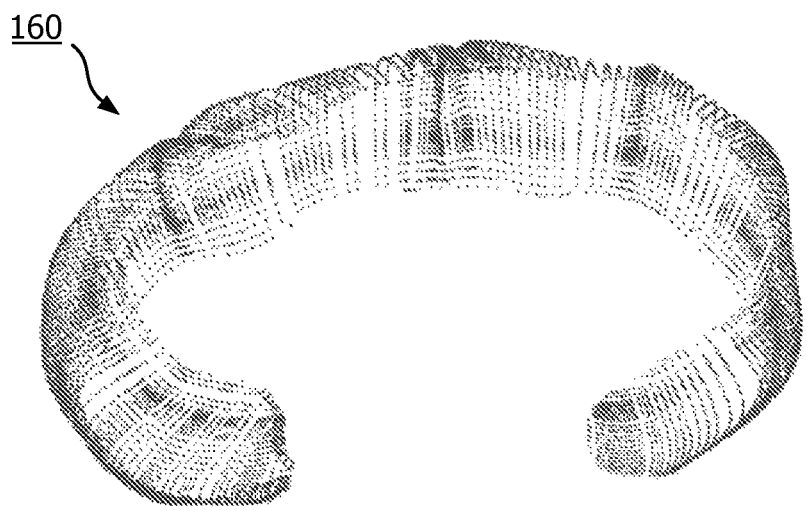

Referring to FIG. 6D, a graph 150 may be displayed to an operator of workstation 120 (FIG. 4) to thereby visualize digitization time periods 152 and 154 of specific sample point(s) and non-digitization time periods 151, 153 and 155 of the remaining sample point(s).

In one embodiment, non-digitization time period 151 represents a pre-scanning positioning of tool pointer 113 relative to the anatomical region with digitization time periods 152 and 154 representing multiple digitized sample points during a line sampling scan of the anatomical organ.

In another embodiment, non-digitization 151 time period represents a pre-scanning positioning of tool pointer 113 relative to the anatomical region with digitization time periods 152 and 154 representing a single digitize sample point during a point sampling scan of the anatomical organ.

Figure 7B:
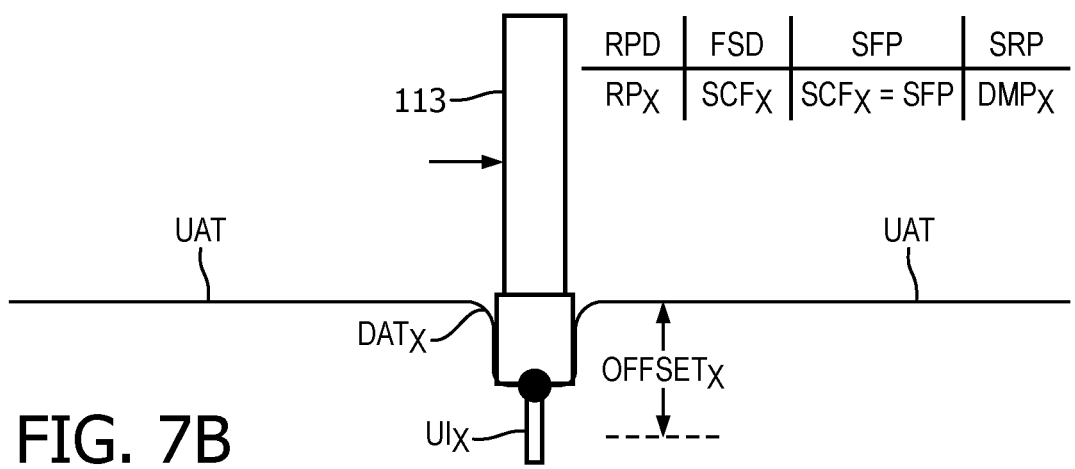
Figure 7C:
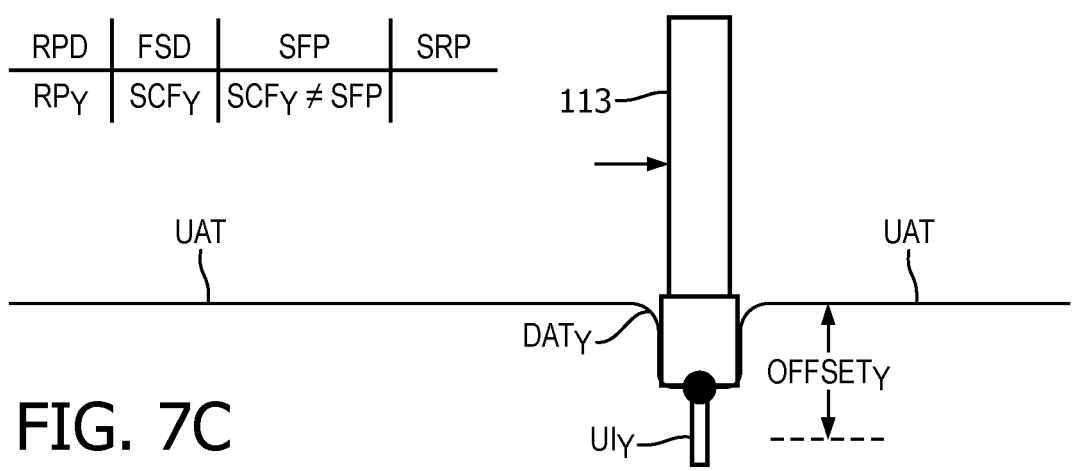

Referring back to FIG. 4, more particular to embodiments of stage S144 utilizing ultrasound laparoscope 114, the navigation of snake scanning robot 110 will result in a digitization of sample points indicating a sensed contact force equating scanned force parameter f as exemplary shown in FIG. 7B and a non-digitization of sample point indicating a sensed contact force not equating scanned force parameter f as exemplary shown in FIG. 7C.

Figure 7D:
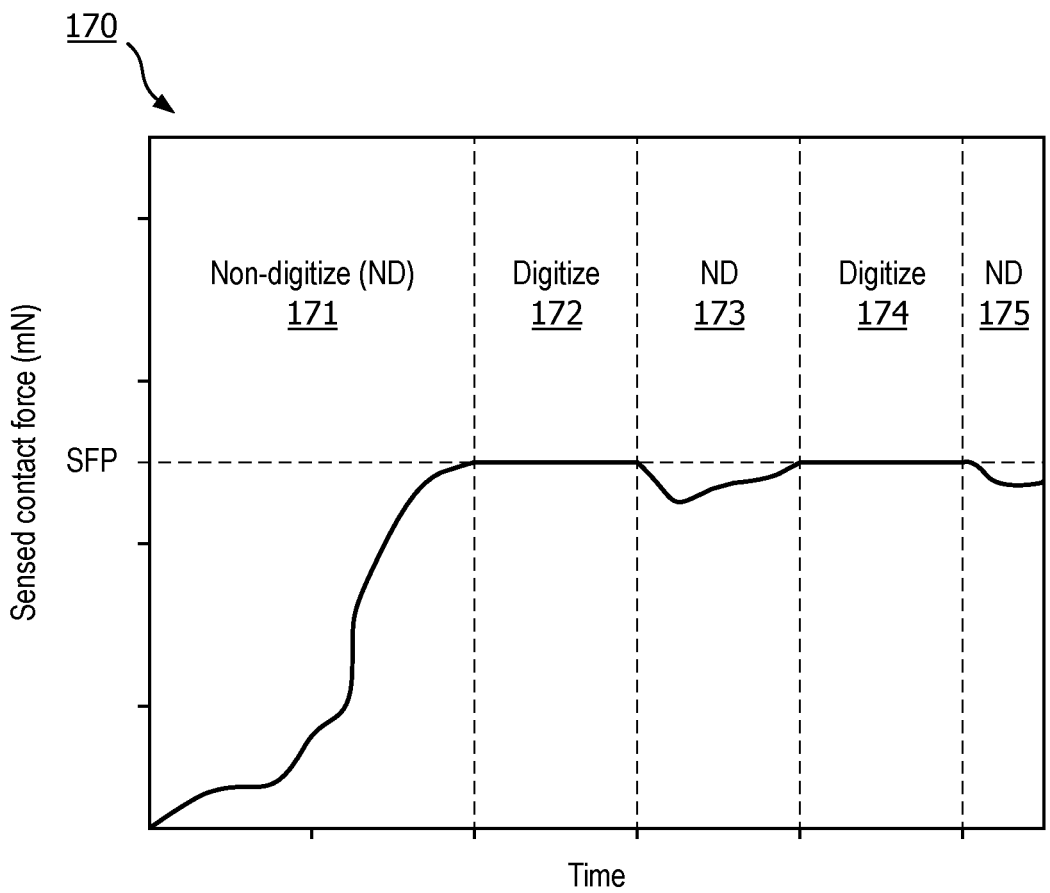
Figure 7E:
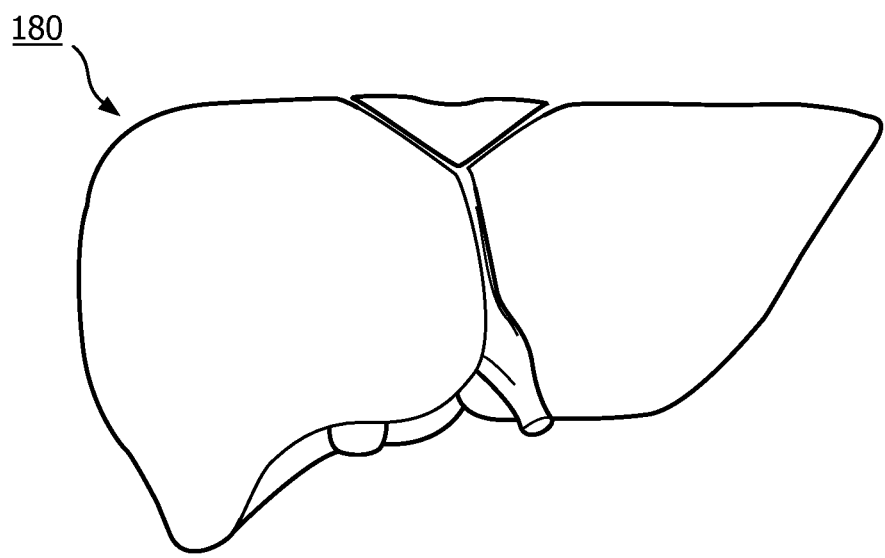

Referring to FIG. 7D, a graph 170 may be displayed to an operator of workstation 120 (FIG. 4) to thereby visualize digitization time periods 172 and 174 of specific sample point(s) and non-digitization time periods 171, 173 and 175 of the remaining sample point(s).

In one embodiment, non-digitization time period 171 represents a pre-scanning positioning of ultrasound laparoscope 114 relative to the anatomical region with digitization time periods 172 and 174 representing multiple digitized sample points during a line sampling scan of the anatomical organ.

In another embodiment, non-digitization 171 time period represents a pre-scanning positioning of ultrasound laparoscope 114 relative to the anatomical region with digitization time periods 172 and 174 representing a single digitize sample point during a point sampling scan of the anatomical organ.

Figure 6F:
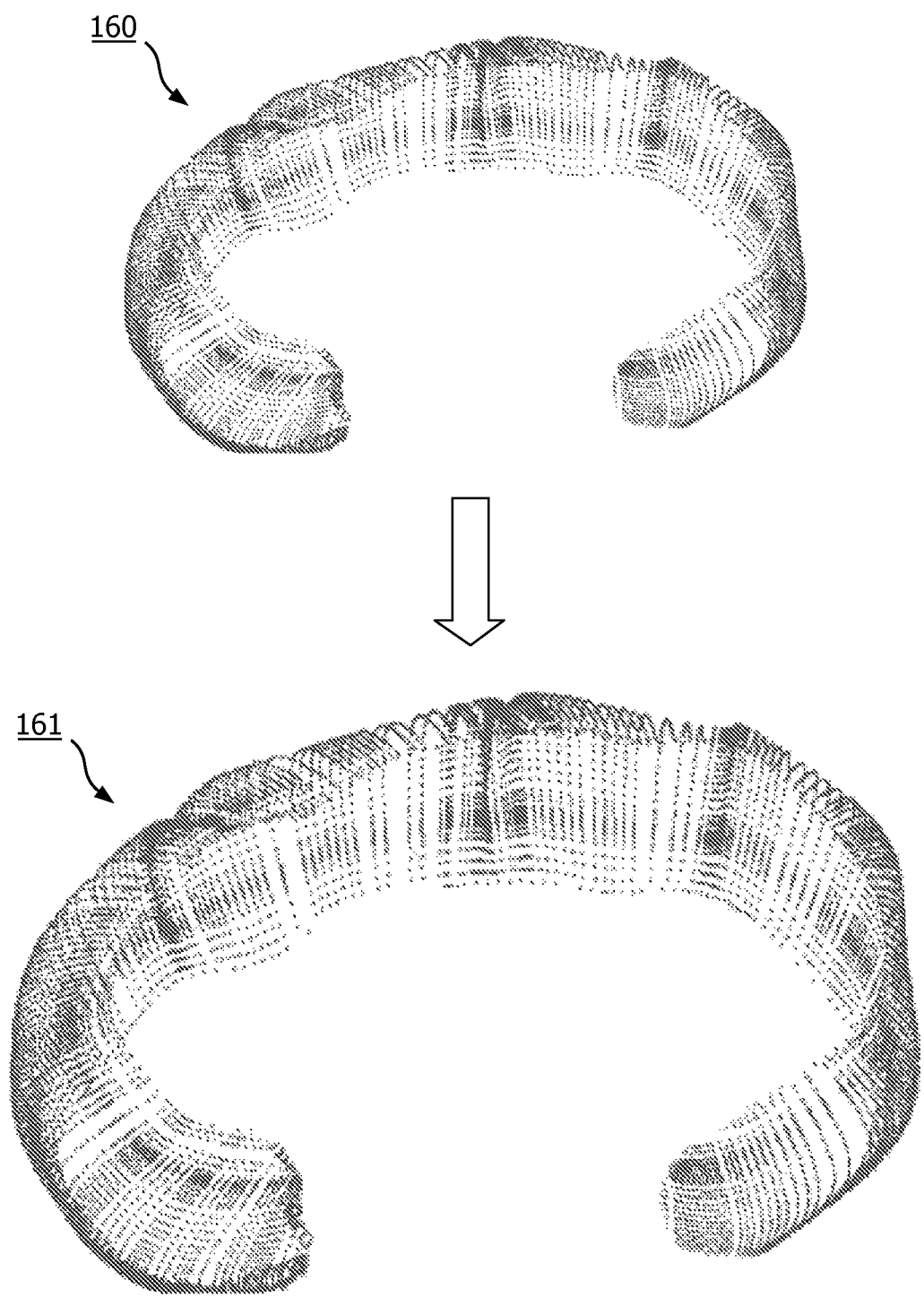
Figure 7F:
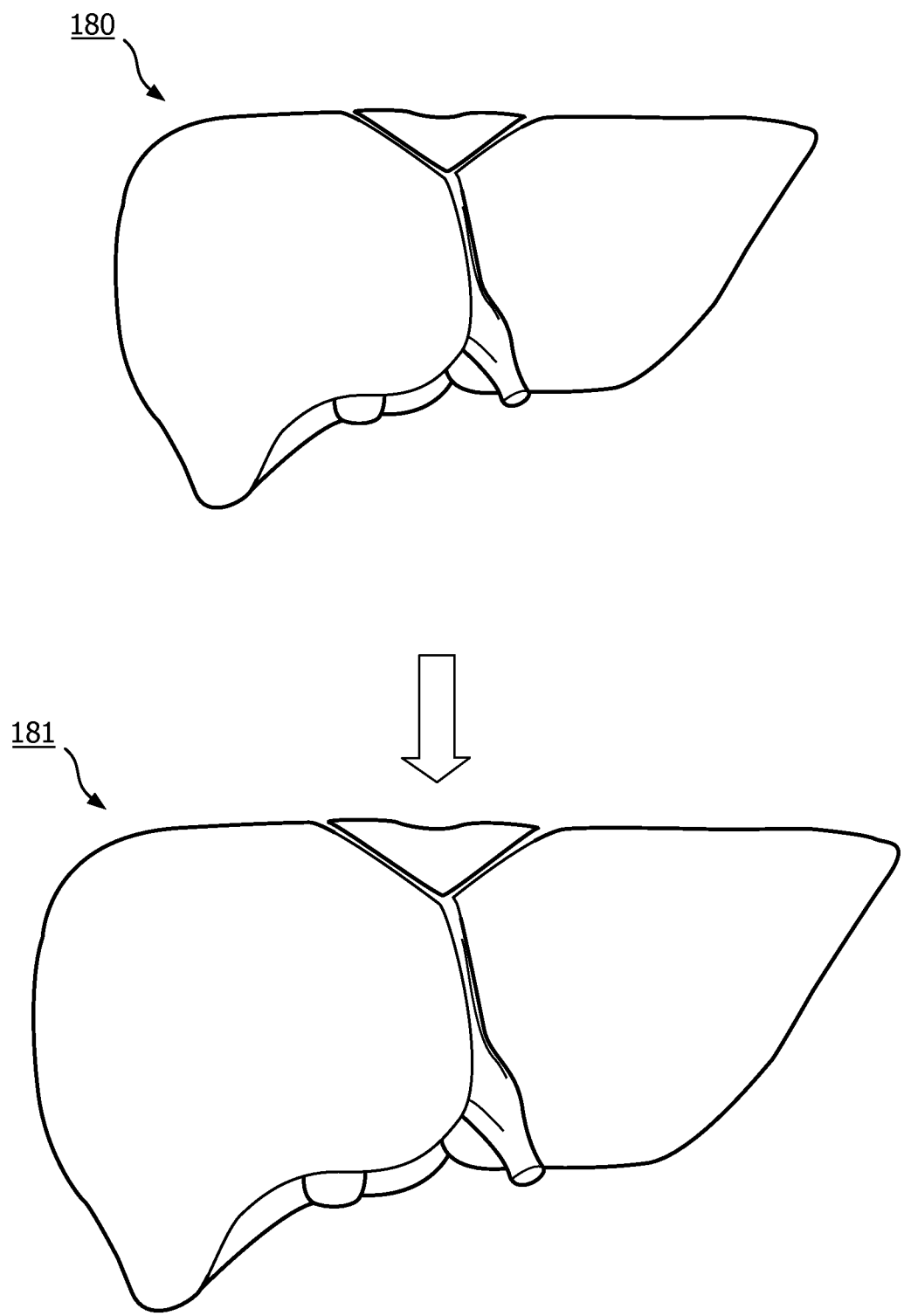

Referring back to FIG. 4, a stage S146 of flowchart 140 encompasses post-scanning activities implemented by model constructor 134 (FIG. 4) and/or model registor 135. These post-scanning activities include, but are not limited to, 1A. model constructor 134 optionally controlling resizing of the intraoperative volume mesh as a function of the defined surface deformation offset as previously described herein in connection with the description of FIGS. 1A and 1B, such as, for example, a resizing of an intraoperative volume mesh 150 to an intraoperative volume mesh 151 as shown in FIG. 6F (note the resizing will normally be in nanometers, thus the resizing as shown in FIG. 6F is exaggerated to visualize the concept); and 2A. model registor 135 registering the unsized/resized intraoperative volume mesh to the preoperative segmented volume model as previously described herein in connection with the description of FIGS. 1A and 1B; or 1B. model constructor 134 optionally controlling resizing of the intraoperative volume image as a function of the defined surface deformation offset as previously described herein in connection with the description of FIGS. 1A and 1B, such as, for example, a resizing of an intraoperative volume image 180 to an intraoperative volume mesh 181 as shown in FIG. 7F (note the resizing will normally be in nanometers, thus the resizing as shown in FIG. 7F is exaggerated to visualize the concept); and 2B. model registor 135 registering the unsized/resized intraoperative volume image to the preoperative segmented volume model as previously described herein in connection with the description of FIGS. 1A and 1B.

Upon completion of stage S146, model fuser 136 implements a fusion technique as known in the art of the present disclosure for generating a registered model fusion 138 as previously described herein whereby display controller 137 controls a display of registered model fusion 138 as shown.

Referring to FIGS. 1-7, those having ordinary skill in the art will appreciate numerous benefits of the present disclosure including, but not limited to, an improvement over surface scanning systems, devices, controllers and methods by the inventions of the present disclosure providing a construction of an intraoperative scanned volume model of an anatomical organ based upon a sensing of a contact force applied by an surface scanning end-effector of a scanning robot to the anatomical organ whereby the contact force is indicative of a defined surface deformation offset of the anatomical organ, thereby enhancing a registration of the intraoperative surface scanned volume model of the anatomical organ with a preoperative image segmented volume model of the anatomical organ.

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk—read only memory (CD-ROM), compact disk—read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive force sensed surface scanning systems, devices, controllers and methods, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A system for force sensed surface scanning, the system comprising:
   a scanning robot including a surface scanning end-effector structurally configured to generate force sensing data informative of a contact force applied by the surface scanning end-effector to an anatomical organ; and
   a surface scanning controller structurally configured to:
      control a surface scanning of the anatomical organ by the surface scanning end-effector, the surface scanning including generation of the force sensing data by the surface scanning end-effector, and
      construct an intraoperative volume model based on the force sensing data indicating a surface deformation offset of the anatomical organ, wherein the surface scanning controller is structurally configured to define the surface deformation offset based on the force sensing data.

2. The system of claim 1, wherein the intraoperative volume model is one of an intraoperative volume mesh or an intraoperative volume image.

3. The system of claim 1, wherein
   the surface scanning controller is further structurally configured to define the surface deformation offset as a function of a viscoelastic property parameter and a scanned force parameter,
   wherein the viscoelastic property parameter quantifies a stiffness of the anatomical organ, and
   wherein the scanned force parameter quantifies a desired contact force for digitizing surface points of the anatomical organ.

4. The system of claim 1, wherein the surface scanning controller is further structurally configured to at least one of:
   define a sampling scan path traversing a preoperative segmented volume model of the anatomical organ, or
   define a sampling scan path having at least one of a geometric pattern traversing the surface of the anatomical organ or a random pattern traversing the surface of the anatomical organ.

5. The system of claim 1, wherein the surface scanning controller is further structurally configured to resize the constructed intraoperative volume model of the anatomical organ as a function of the defined surface deformation offset.

6. The system of claim 1, wherein the surface scanning controller is further structurally configured to register the constructed intraoperative volume model of the anatomical organ and a preoperative segmented volume model of the anatomical organ.

7. The system of claim 1, wherein:
   the force sensing data is informative of a contact force applied by the surface scanning end-effector to a plurality of sample points of the anatomical organ; and
   the surface scanning controller is structurally configured to construct the intraoperative volume model to include each sample point of the plurality of sample points having a contact force applied thereto by the surface scanning end-effector during the surface scanning indicating the surface deformation offset and excluding each sample point of the plurality of sample points having a contact force applied thereto by the surface scanning end-effector during the surface scanning failing to indicate the surface deformation offset.

8. A controller for force sensed surface scanning, the controller comprising:
   a memory that stores instructions; and
   a processor structurally configured to execute the instructions and, when executed by the processor, the instructions cause the processor to:
      control a surface scanning of an anatomical organ by a surface scanning end-effector of a scanning robot, the surface scanning including generation, by the surface scanning end-effector, of force sensing data informative of a contact force applied by the surface scanning end-effector to the anatomical organ, and
      construct an intraoperative volume model based on the force sensing data indicating a surface deformation offset of the anatomical organ, wherein the processor is further structurally configured to define the surface deformation offset based on the force sensing data.

9. The controller of claim 8, wherein
the processor is further structurally configured to define the surface deformation offset as a function of a viscoelastic property parameter and a scanned force parameter,
wherein the viscoelastic property parameter quantifies a stiffness of the anatomical organ, and
wherein the scanned force parameter quantifies a desired contact force for digitizing surface points of the anatomical organ.

10. The controller of claim 8, wherein the processor is further structurally configured to at least one of:
define a sampling scan path traversing a preoperative segmented volume model of the anatomical organ, or
define a sampling scan path having at least one of a geometric pattern traversing the surface of the anatomical organ or a random pattern traversing the surface of the anatomical organ.

11. The controller of claim 8, wherein the processor is further structurally configured to resize a constructed intraoperative volume model of the anatomical organ as a function of the defined surface deformation offset.

12. The controller of claim 8, wherein:
the force sensing data is informative of a contact force applied by the surface scanning end-effector to a plurality of sample points of the anatomical organ; and
the surface scanning controller is structurally configured to construct the intraoperative volume model to include each sample point of the plurality of sample points having a contact force applied thereto by the surface scanning end-effector during the surface scanning indicating the surface deformation offset and excluding each sample point of the plurality of sample points having a contact force applied thereto by the surface scanning end-effector during the surface scanning failing to indicate the surface deformation offset.

13. A method of force sensed surface scanning, the method comprising:
controlling a surface scanning of an anatomical organ by a surface scanning end-effector of a scanning robot, the surface scanning including generation, by the surface scanning end-effector, of force sensing data informative of a contact force applied by the surface scanning end-effector to the anatomical organ; and
constructing an intraoperative volume model based on the force sensing data indicating a surface deformation offset of the anatomical organ, wherein the surface deformation offset is defined based on the force sensing data.

14. The method of claim 13, further comprising:
defining the surface deformation offset as a function of a visoelastic property parameter and a scanned force parameter,
wherein the viscoelastic property parameter quantifies a stiffness of the anatomical organ, and
wherein the scanned force parameter quantifies a desired contact force for digitizing surface points of the anatomical organ.

15. The method of claim 13, further comprising:
delineating a sampling scan path on a preoperative segmented volume model of the anatomical organ.

16. The method of claim 13, further comprising:
resizing a constructed intraoperative volume model of the anatomical organ as a function of the defined surface deformation offset of the anatomical organ.

17. The method of claim 13,
wherein the force sensing data is informative of a contact force applied by the surface scanning end-effector to a plurality of sample points of the anatomical organ; and
the force sensed surface scanning method further comprising constructing the intraoperative volume model to include each sample point of the plurality of sample points having a contact force applied thereto by the surface scanning end-effector during the surface scanning indicating the surface deformation offset and excluding each sample point of the plurality of sample points having a contact force applied thereto by the surface scanning end-effector during the surface scanning failing to indicate the surface deformation offset.

* * * * *